United States Patent
Chen

(10) Patent No.: US 11,162,147 B2
(45) Date of Patent: Nov. 2, 2021

(54) APPARATUSES AND METHODS FOR DETECTING NUCLEIC ACIDS

(71) Applicant: Shengxi Chen, Chandler, AZ (US)

(72) Inventor: Shengxi Chen, Chandler, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/431,678

(22) Filed: Jun. 4, 2019

(65) Prior Publication Data
US 2019/0382855 A1  Dec. 19, 2019

Related U.S. Application Data

(60) Provisional application No. 62/680,752, filed on Jun. 5, 2018.

(51) Int. Cl.
*C12Q 1/70* (2006.01)
*G01N 21/76* (2006.01)

(52) U.S. Cl.
CPC ............. *C12Q 1/701* (2013.01); *G01N 21/76* (2013.01)

(58) Field of Classification Search
CPC ................................ C12Q 1/701; G01N 21/76
See application file for complete search history.

(56) References Cited

U.S. PATENT DOCUMENTS

| | | | |
|---|---|---|---|
| 10,100,091 B2 | 10/2018 | Chen | |
| 2011/0008797 A1* | 1/2011 | Zilch | H01F 1/0063 435/6.14 |
| 2018/0371526 A1 | 12/2018 | Chen et al. | |

FOREIGN PATENT DOCUMENTS

| | | | |
|---|---|---|---|
| JP | 2017-223582 | * | 12/2017 |
| WO | 2015057688 A2 | | 4/2015 |

OTHER PUBLICATIONS

Lou et al, Detection of DNA Point Mutation by Atom Transfer Radical Polymerization, 2005, Anal. Chem., 77, 4698-4705. (Year: 2005).*
Lou et al 2007, Core-Shell Au Nanoparticle Formation with DNA-Polymer Hybrid Coatings Using Aqueous ATRP, 2007, Biomacromolecules, 8, 1385-1390. (Year: 2007).*
JP 2017-223582, CLAIMS—Machine translation from Japanese to English, pp. 1-3, printed on Sep. 24, 2020. (Year: 2020).*
JP 2017-223582, Description—Machine translation from Japanese to English, pp. 1-16, printed on Sep. 24, 2020. (Year: 2020).*
U.S. Appl. No. 16/431,678 structure search results, pp. 1-98, printed Sep. 24, 2020 (Year: 2020).*
Alter, H. et al., "Evaluation of branched DNA signal amplification for the detection of hepatitis C virus RNA", Journal of Viral Hepatitis, May 1995, vol. 2, No. 3, pp. 121-132 <DOI:10.1111/j.1365-2893.1995.tb00017.x>.
Callahan, J. et al., "Development and Evaluation of Serotype- and Group-Specific Fluorogenic Reverse Transcriptase PCR (TaqMan) Assays for Dengue Virus", Journal of Clinical Microbiology, Nov. 2001, vol. 39, No. 11, pp. 4119-4124 <DOI:10.1128/JCM.39.11.4119-4124.2001 >.
Collins, M. et al., "A branched DNA signal amplification assay for quantification of nucleic acid targets below 100 molecules/ml". Nucleic Acids Research, Aug. 1997, vol. 25, No. 15, pp. 2979-2984 <DOI:10.1093/nar/25.15.2979>.
Cristina, J. et al., "Genetic variability and molecular evolution of Hepatitis A virus", Virus Research, Aug. 2007 (available online Feb. 2007), vol. 127, No. 2, pp. 151-157 <DOI:10.1016/j.virusres.2007.01.005>.
Das, J. et al., "An electrochemical clamp assay for direct, rapid analysis of circulating nucleic acids in serum", Nature Chemistry, Jun. 2015, vol. 7, pp. 569-575 <DOI:10.1038/nchem.2270>.
Fu, C. et al., "A signal-on homogeneous electrochemical biosensor for sequence-specific microRNA based on duplex-specific nuclease-assisted target recycling amplification", Analytical Methods, Aug. 2016, vol. 8, No. 39, pp. 7034-7039 <DOI:10.1039/C6AY02039A>.
Guzman, M. et al., "Dengue: a continuing global threat", Nature Reviews Microbiology, Dec. 2010, vol. 8, pp. S7-S16 <DOI:10.1038/nrmicro2460>.
Kwakye, S. et al., "Electrochemical microfluidic biosensor for nucleic acid detection with integrated minipotentiostat", Biosensors and Bioelectronics, Jun. 2006 (available online Jan. 2006), vol. 21, No. 12, pp. 2217-2223 <DOI:10.1016/j.bios.2005.11.017>.
Lagier, M. et al., "An electrochemical RNA hybridization assay for detection of the fecal indicator bacterium *Escherichia coli*", Marine Pollution Bulletin, Nov. 2005 (available online May 2005), vol. 50, No. 11, pp. 1251-1261 <DOI: 10.1016/j.marpolbul.2005.04.034>.
Lanciotti, R. et al., "Rapid detection and typing of dengue viruses from clinical samples by using reverse transcriptase-polymerase chain reaction", Journal of Clinical Microbiology, Mar. 1992, vol. 30, No. 3, pp. 545-551.
Lee, J. et al., "Sensitive and Selective Detection of HIV-1 RRE RNA Using Vertical Silicon Nanowire Electrode Array", Nanoscale Research Letters, Jul. 2016, vol. 11, No. 341, 7 pages <DOI:10.1186/s11671-016-1504-8>.
Martell, M. et al., "Structural analysis of hepatitis C RNA genome using DNA microarrays", Nucleic Acids Research, Jun. 2004 (available online Jan. 2004), vol. 32, No. 11, article e90, 12 pages <DOI:10.1093/nar/gnh088>.
McCauley, J. et al., "Structure and function of the influenza virus genome",Biochemical Journal, May 1983, vol. 211, No. 2, pp. 281-294 <DOI:10.1042/bj2110281>.

(Continued)

*Primary Examiner* — Narayan K Bhat
(74) *Attorney, Agent, or Firm* — Byrne Poh LLP; Nina R. Horan

(57) ABSTRACT

The present disclosure provides a low cost, high sensitivity, high specificity and rapid diagnostic apparatus and method to detect nucleic acids in a sample at room temperature. As low as tens of copies of nucleic acids can be detected without any additional equipment.

9 Claims, 7 Drawing Sheets
Specification includes a Sequence Listing.

(56) References Cited

OTHER PUBLICATIONS

Mei, J. et al., "Aggregation-Induced Emission: Together We Shine, United We Soar!", Chemical Reviews, Oct. 2015, vol. 115, No. 21, pp. 11718-11940 <DOI:10.1021/acs.chemrev.5b00263>.

Sharma, A. et al., "Zika Virus: Transmission, Detection, Control, and Prevention", Frontiers in Microbiology, Feb. 2017, vol. 8, No. 110, 14 pages <DOI:10.3389/fmicb.2017.00110>.

Shu, P-Y. et al., "Current Advances in Dengue Diagnosis", Clinical and Diagnostic Laboratory Immunology, Jul. 2004, vol. 11, No. 4, pp. 642-650 <DOI:10.1128/CDLI.11.4.642-650.2004>.

Watts, J. et al., "Architecture and secondary structure of an entire HIV-1 RNA genome", Nature, Aug. 2009, vol. 460, pp. 711-716 <DOI:10.1038/nature08237>.

Wu, J. et al., "Ternary Surface Monolayers for Ultrasensitive (Zeptomole) Amperometric Detection of Nucleic Acid Hybridization without Signal Amplification", Analytical Chemistry, Sep. 2010, vol. 82, No. 21, pp. 8830-8837 <DOI:10.1021/ac101474k>.

Wu, S-J. et al., "Detection of Dengue Viral RNA Using a Nucleic Acid Sequence-Based Amplification Assay", Journal of Clinical Microbiology, Aug. 2001, vol. 39, No. 8, pp. 2794-2798 <DOI:10.1128/JCM.39.8.2794-2798.2001>.

U.S. Appl. No. 16/804,691, Hecht et al., filed Feb. 28, 2020.

\* cited by examiner

APPARATUSES AND METHODS FOR DETECTING NUCLEIC ACIDS

FEDERALLY SPONSORED RESEARCH OR DEVELOPMENT

This invention was made with government support under W81XWH-16-1-0141 awarded by the ARMY/MRMC. The government has certain rights in the invention.

SEQUENCE LISTING

The present disclosure contains a Sequence Listing that has been submitted in ASCII format via EFS-Web and is hereby incorporated by reference in its entirety. The ASCII copy, created on Aug. 16, 2019, is named 0118090.203-US2.txt, and is 1,361 bytes in size.

BACKGROUND

Ribonucleic acid (RNA) plays a central role in almost all living organisms, including mammals, bacteria, protozoa, mycoplasma, chlamydia, viruses, etc.[1] RNA often transfers genetic information from DNA to proteins. Based on their function, RNAs were classified as messenger RNA (mRNA), transfer RNA (t), ribosomal RNA (r), and small nuclear RNA (sno), among others. In some kinds of viruses, such as HIV,[2] dengue,[3] Zika,[4] hepatitis A,[5] hepatitis C,[6] and influenza viruses,[7] RNA plays the role of sole genetic carrier. Detection of the presence or overexpression of specific RNAs has been used in a wide range of clinical diagnostics, as well as in environmental and food analysis.[1]

For efficient and accurate detection of RNA, the traditional method is to amplify copies of nucleic acid to generate a detectable signal. A few studies have used two-step nested reverse transcription polymerase chain reactions (RT-PCR) to achieve a highly effective detection of viral RNAs using an agarose gel.[8,9] More recently, real-time RT-PCR detection assays have been developed to provide greater rapidity, specificity, sensitivity, and easier standardization for the diagnosis of viral RNAs.[8,10] Both the nested RT-PCR and real-time RT-PCR methods require multiple thermocycling steps, which is time-consuming and needs special thermocycling equipment. To avoid these multiple thermocycling steps, a nucleic acid sequence-based amplification (NASBA) assay, which is a single-step isothermal RNA amplification system, has been used to detect RNAs.[11] Even though the NASBA assay requires only a single thermocycling step, a single melting step at about 60° C. and an amplification reaction at 41° C. still require special temperature control equipment. These RT-PCR reactions amplify the target RNA up to $10^9$ copies in several hours. After that, these RT-PCR products must be detected by ethidium bromide staining, a fluorescent DNA probe or a ruthenium-labeled DNA probe, which require additional equipment in a laboratory setting. The RT-PCR-based detection is a highly efficient diagnostic method that can be finished in 1-2 days. Both the sensitivity and specificity of this method are >95%. However, a RT-PCR reaction requires more than two oligonucleotide primers, two to three enzymes, 4-8 kinds of nucleotides, and several associated materials. Thus, the cost of each test is rather high. More importantly, a RT-PCR-based diagnosis requires special temperature-control and signal-detection equipment, and 1-2 days for the detection results. Therefore, it is not suitable for point-of-care applications for clinical diagnostics, nor for use in the field of environmental and food analysis.

To develop a nucleic acid amplification-free method for RNA detection, various electrochemical techniques have been used to amplify detectable signals.[12-15] In general, the transduction element of an electrochemical biosensor is an electrode (e.g., silicon nanowire,[12] graphite electrode,[13] indium tin oxide electrode,[14] or gold-coated electrode[15]); a DNA oligonucleotide probe immobilized on the surface of the electrode captures desired RNA via DNA/RNA hybridization; the hybridized RNA results in a specific binding of another substance (e.g., antibody, lectin, DNA, or aptamer) to generate changes of interfacial properties of the electrode; the signals of property changes are amplified by non-covalent binding of redox indicators (e.g., intercalators or groove binders), covalent redox labels (e.g., nanoparticles, metal chelates or organometallics) or reporter enzymes (e.g., peroxidases or phosphatases); the amplified signals are measured using electrical equipment.[1,12-15] These electrochemical techniques have been developed for a wide range of detection of rRNAs, mRNAs, microRNAs and viral RNAs.[1] These procedures don't require amplification of nucleic acid and can achieve detection results in 1~5 h. However, the detection limit of these methods ranges from 40 zmol to 10 nmol copies of RNAs, which is not sensitive enough to detect some kinds of pathogens or disease markers.[16,17]

To increase sensitivity, a branched DNA (bDNA) technology has been used to detect viral RNAs.[18,19] In this method, multiple copies of capture probes, capture extenders, branched DNAs, or alkaline phosphatase-labeled DNA probes are used for binding to multiple sites of viral RNA. Multiple copies of DNA probes increase the sensitivity of the detection, and the limit of this detection is low to 50 copies of viral RNA for each assay.[19] However, the DNA probes used to capture each kind of RNA make it complicated and quite expensive. In addition, these methods also need special temperature-control equipment for DNA/RNA hybridization and specific signal-detection equipment for analysis of the RNA detection results.

Citation of any reference in this section is not to be construed as an admission that such reference is prior art to the present disclosure.

SUMMARY

The present disclosure provides a low cost, high sensitivity, high specificity and rapid diagnostic apparatus and method to detect nucleic acids in a sample at room temperature. As low as tens of copies of nucleic acids can be detected without any additional equipment.

DETAILED DESCRIPTION

Figure 1:
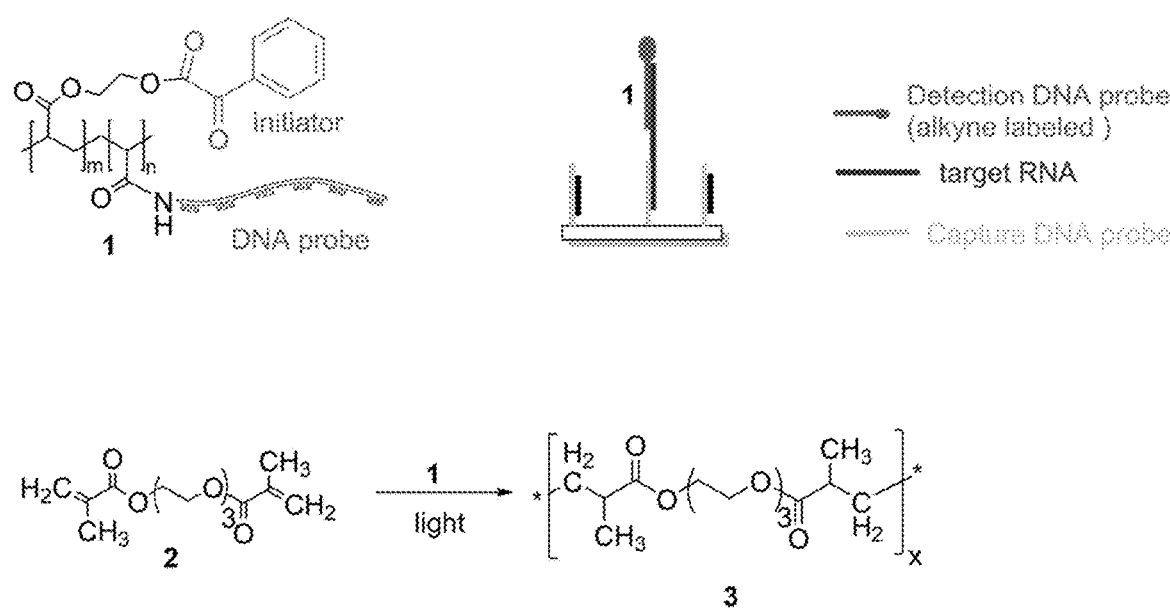
FIG. 1 provides a schematic diagram of a method to detect RNA according to one embodiment of the present disclosure.

Certain illustrative embodiments include the following:

1. A nanoparticle comprising:
   (a) a radical initiator;
   (b) a detector DNA, wherein the sequence of the detector DNA strand is partially complementary to a first portion of sequence of a target nucleic acid;

2. The nanoparticle of the above 1, further comprising:
   (c) a target nucleic acid, wherein the first portion of the target nucleic acid sequence partially hybridizes to the detector DNA sequence.

3. The nanoparticle of the above 2, further comprising:
   (d) a capture DNA probe, wherein the sequence of the capture DNA probe is partially complementary to a second portion of the target nucleic acid sequence.

4. The nanoparticle of any one of the above 1 to 3, wherein the nanoparticle comprises gold.

5. The nanoparticle of any one of the above 1 to 4, wherein the radical initiator comprises a thiol 6. The nanoparticle of any one of the above 1 to 5, wherein the radical initiator is 2-mercaptoethyl 2-oxo-2-phenylacetate.

7. The nanoparticle of any one of the above 1 to 6, wherein the nucleic acid is RNA.

8. The nanoparticle of any one of the above 1 to 6, wherein the nucleic acid is DNA.

9. A method for preparing a nanoparticle, the method comprising:
   (a) attaching a radical initiator to a nanoparticle;
   (b) attaching a detector DNA to the nanoparticle, wherein the sequence of the detector DNA is partially complementary to a first portion of a target nucleic acid.

10. The method of the above 9, further comprising:
    (c) contacting the nanoparticle of step (b) with a target nucleic acid, wherein the target nucleic acid partially hybridizes to the detector DNA.

11. The method of the above 10, further comprising:
    (d) contacting the nanoparticle of step (c) with a capture DNA probe, wherein the sequence of the capture DNA probe is partially complementary to a second portion of the target nucleic acid sequence.

12. The method of any one of the above 9 to 11, wherein the nucleic acid is RNA. 13. The method of any one of the above 9 to 11, wherein the nucleic acid is DNA. 14. An apparatus comprising:
    (a) a surface for attaching a DNA capture probe;
    (b) the capture DNA probe;
    (c) a target nucleic acid, wherein a first portion of the target nucleic acid sequence is partially complementary to the sequence of the capture DNA probe; and
    (d) a nanoparticle comprising (i) a radical initiator; and (ii) a detector DNA, wherein the sequence of the detector DNA strand is partially complementary to a second portion of sequence of a target nucleic acid.

15. The apparatus of the above 14, wherein the surface for attaching the DNA capture probe is glass.

16. The apparatus of the above 15, further comprising a monomer comprising a moiety selected from the group consisting of an ethylene group, fluoroethylene group, vinyl chloride group, styrene group, and epoxide group.

17. The apparatus of the above 16, wherein the monomer is a compound of formula 9, as herein described.

18. The apparatus of the above 16, wherein the monomer is (ethane-1,2-diylbis(oxy))bis(ethane-2, 1-diyl) bis(2-methylacrylate).

19. The apparatus of the above 15, further comprising a polymer. 20. The apparatus of the above 19, wherein the polymer is a fluorescent polymer. 21. The apparatus of the above 20, wherein the polymer is a compound of formula 10, as herein described.

22. The apparatus of the above 19, wherein the polymer is prepared from (ethane-1, 2-diylbis(oxy))bis(ethane-2,1-diyl) bis(2-methylacrylate).

23. The apparatus of any one of the above 14 to 22, wherein the target nucleic acid is RNA.

24. The apparatus of any one of the above 14 to 22, wherein the target nucleic acid is DNA.

25. A method for preparing an apparatus for detecting nucleic acid, the method comprising:
    (a) attaching a capture DNA probe to a surface, wherein the capture DNA probe comprises a functional group capable of attaching to the surface and comprises a sequence that is partially complementary to a first portion of a sequence of target nucleic acid;
    (b) contacting the target RNA with the capture DNA probe attached to the surface from step (a), wherein the first portion of the target nucleic acid partially hybridizes to the capture DNA probe; and
    (c) contacting a nanoparticle with the product of step (b), wherein the nanoparticle comprises a radical initiator and a detector DNA probe, the detector DNA probe comprising a sequence that is partially complementary to a second portion of the sequence of target nucleic acid, and wherein the detector DNA probe of the nanoparticle partially hybridizes to the second portion of the target nucleic acid.

26. The method of the above 25, wherein the nucleic acid is RNA.

27. The method of the above 25, wherein the nucleic acid is DNA.

28. A method for detecting nucleic acid in a sample, the method comprising:
    (a) contacting a monomer with the apparatus of the above 14;

(b) exposing the product of step (a) to light; and (c) detecting the presence of a polymer, wherein the presence of polymer indicates nucleic acid in the sample.

29. The method of the above 28, wherein the nucleic acid is RNA.

30. The method of the above 28, wherein the nucleic acid is DNA.

31. The method of the above 28, wherein the polymer is fluorescent.

32. A compound of formula (I):

A-B-C    (I), wherein:
A is an initiator;
B is a linker; and
C is a detector DNA probe, the DNA detector probe comprising a sequence that is capable of partially hybridizing to a target nucleic acid.

33. An apparatus comprising:
(a) a surface for attaching a DNA capture probe;
(b) the capture DNA probe;
(c) a target nucleic acid, wherein a portion of the target nucleic acid sequence is partially complementary to the sequence of the capture DNA probe; and
(d) the compound of the above 32.

34. The apparatus of the above 33, wherein the surface for attaching the DNA capture probe is glass.

35. The apparatus of the above 33, further comprising a monomer comprising a moiety selected from the group consisting of an ethylene group, fluoroethylene group, vinyl chloride group, styrene group, and epoxide group.

36. The apparatus of the above 35, wherein the monomer is a compound of formula 9.

37. The apparatus of the above 35, wherein the monomer is (ethane-1,2-diylbis(oxy))bis(ethane-2, 1-diyl) bis(2-methylacrylate).

38. The apparatus of the above 29, further comprising a polymer.

39. The apparatus of the above 33, wherein the polymer is compound of formula 10.

40. The apparatus of the above 33, wherein the polymer is prepared from (ethane-1, 2-diylbis(oxy))bis(ethane-2,1-diyl) bis(2-methylacrylate).

41. The apparatus of any one of the above 33 to 40, wherein the target nucleic acid is RNA.

42. The apparatus of any one of the above 33 to 40, wherein the target nucleic acid is DNA.

43. A method for preparing an apparatus for detecting nucleic acids, the method comprising:
(a) attaching a capture DNA probe to a surface, wherein the capture DNA probe comprises a functional group capable of attaching to the surface and comprises a sequence that is partially complementary to a first portion of a sequence of target nucleic acid;
(b) contacting the target nucleic acid with the capture DNA probe attached to the surface from step (a), wherein the first portion of the target nucleic acid partially hybridizes to the capture DNA probe; and
(c) contacting the compound of the above 32 with the product of step (b), wherein the detector DNA probe partially hybridizes to the second portion of the target nucleic acid.

44. The method of the above 43, wherein the nucleic acid is RNA.

45. The method of the above 43, wherein the nucleic acid is DNA.

46. A method for detecting nucleic acid in a sample, the method comprising:
(a) contacting a monomer with the apparatus of the above 33;
(b) exposing the product of step (a) to light; and
(c) detecting the presence of a polymer, wherein the presence of polymer indicates nucleic acid in the sample.

47. The method of the above 46, wherein the polymer is fluorescent.

48. The method of the above 46, wherein the nucleic acid is RNA.

49. The method of the above 46, wherein the nucleic acid is DNA.

Definitions

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The term "$(C_1-C_6)$ alkyl" refers to a saturated hydrocarbon structure having 1, 2, 3, 4, 5 or 6 carbon atoms. When an alkyl residue having a specific number of carbon atoms is stated, it is intended that all geometric isomers having that number of carbon atoms are encompassed. Examples of $(C_1-C_6)$ alkyl include methyl, ethyl, n-propyl, iso-propyl, n-butyl, iso-butyl, tert-butyl, n-pentyl, n-hexyl, and the like.

The term "$(C_1-C_{20})$ alkyl" refers to a saturated hydrocarbon structure having 1, 2, 3, 4, 5, 6, 7, 8, 9, 10, 11, 12, 13, 14, 15, 16, 17, 18, 19, or 20 carbon atoms. When an alkyl residue having a specific number of carbon atoms is stated, it is intended that all geometric isomers having that number of carbon atoms are encompassed. Examples of $(C_1-C_{20})$ alkyl include methyl, ethyl, n-propyl, iso-propyl, n-butyl, iso-butyl, tert-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosanyl and the like.

The term "$(C_2-C_6)$ alkynyl" refers to an unsaturated hydrocarbon structure having 2, 3, 4, 5 or 6 carbon atoms and having at least one carbon-carbon triple bond. Examples of $(C_2-C_6)$ alkynyl include prop-1-yne, but-1-yne, but-2-yne, pent-1-yne, pent-2-yne, 3-methylbut-1-yne, 3-methylpent-1-yne, hex-2-yne and the like.

The term "$(C_1-C_{20})$ polyhydroxy alkyl" refers to a $(C_1-C_{20})$ alkyl having at least one —OH group. The term "$(C_1-C_6)$ polyhydroxy alkyl" refers to a $(C_1-C_6)$ alkyl having at least one —OH group. The term "$(C_1-C_{20})$ polyamino alkyl" refers to a $(C_1-C_{20})$ alkyl having at least one —NH$_2$ group. The term "($C_1$-$C_6$) polyamino alkyl" refers to a ($C_1$-$C_6$) alkyl having at least one —$NH_2$ group.

The term "carbohydrate" refers to a monosaccharide, disaccharide, oligosaccharide and polysaccharide. Examples of carbohydrates include glucose, fructose, galactose, sucrose and lactose and their derivatives.

Nanoparticles, Methods for Preparing Them, Apparatuses Comprising Them, and Methods of Using Them The present disclosure provides nanoparticles for detecting nucleic acids. The nanoparticle comprises (a) a radical initiator; and (b) a detector DNA, wherein the sequence of the detector DNA strand is partially complementary to a first portion of sequence of a target nucleic acid.

In some embodiments, the nanoparticle further comprises (c) a target nucleic acid, wherein the first portion of the target nucleic acid sequence partially hybridizes to the detector DNA sequence.

In some embodiments, the nanoparticle further comprises (d) a capture DNA probe, wherein the sequence of the capture DNA probe is partially complementary to a second portion of the target nucleic acid sequence.

The nanoparticle comprises a material selected from the group consisting of gold, silver, iron, and carbon. In one embodiment, the nanoparticle comprises gold.

The radical initiator comprises a functional group for attachment to the nanoparticle. The functional group is selected from the group consisting of thiol, amine, hydroxy, and carboxyl. In one embodiment, the radical initiator comprises a thiol.

Examples of suitable radical initiators include, but are not limited to, 2-mercaptoethyl 2-oxo-2-phenylacetate, halogens, Azo compounds (R—N=N—R'), di-tert-butyl peroxide, benzoyl peroxide (($PhCOO)_2$). In one embodiment, the radical initiator is 2-mercaptoethyl 2-oxo-2-phenylacetate.

The present disclosure also provides methods for preparing nanoparticles as herein described. The method comprises (a) attaching a radical initiator to a nanoparticle; (b) attaching a detector DNA to the nanoparticle, wherein the sequence of the detector DNA is partially complementary to a first portion of a target nucleic acid.

In some embodiments, the method further comprises (c) contacting the nanoparticle of step (b) with a target nucleic acid, wherein the target nucleic acid partially hybridizes to the detector DNA.

In some embodiments, the method further comprises (d) contacting the nanoparticle of step (c) with a capture DNA probe, wherein the sequence of the capture DNA probe is partially complementary to a second portion of the target nucleic acid sequence.

The present disclosure provides an apparatus for detecting nucleic acids. The apparatus comprises (a) a surface for attaching a DNA capture probe; (b) the capture DNA probe; (c) a target nucleic acid, wherein a first portion of the target nucleic acid sequence is partially complementary to the sequence of the capture DNA probe; and (d) a nanoparticle comprising (i) a radical initiator; and (ii) a detector DNA, wherein the sequence of the detector DNA strand is partially complementary to a second portion of sequence of a target nucleic acid.

The surface for attaching the DNA capture probe is any surface capable of attaching DNA. Suitable surfaces that may be used include, but are not limited to, glass, nitrocellulose membrane, polyvinylidene fluoride membrane, and cellulose paper. In one embodiment, the surface for attaching the DNA capture probe is glass.

In some embodiments, the apparatus further comprises a monomer comprising a moiety selected from the group consisting of an ethylene group, fluoroethylene group, vinyl chloride group, styrene group, and epoxide group. The monomer is any compound that can form a polymer. A suitable monomer is (ethane-1, 2-diylbis(oxy))bis(ethane-2, 1-diyl) bis(2-methylacrylate). Another suitable monomer is a compound of formula 9:

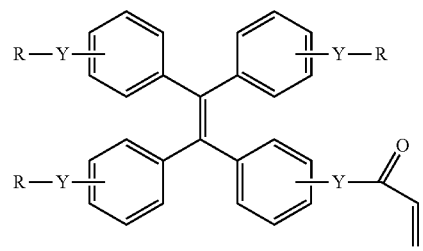

9 wherein,

Y is independently selected from O, S, NH or $NR_1$;

R is independently selected from H, ($C_2$-$C_6$) alkyne, $R^2SO_3$, ($C_1$-$C_{20}$) polyhydroxy alkyl, ($C_1$-$C_{20}$) polyamino alkyl or carbohydrate.

$R_1$ and $R_2$ are independently H or ($C_1$-$C_6$) alkyl.

In one embodiment, Y is O, S or NH. In another embodiment, Y is O. In another embodiment, Y is S. In another embodiment, Y is NH. In another embodiment, Y is $NR_1$.

In one embodiment, R is H, $R_2SO_3$ or a carbohydrate. In another embodiment, R is H. In another embodiment, R is $R_2SO_3$. In another embodiment, R is a carbohydrate. In some embodiments in which R is a carbohydrate, the carbohydrate is glucose, fructose, galactose, sucrose and lactose and their derivatives.

In one embodiment, R is ($C_1$-$C_{20}$) polyhydroxy alkyl or ($C_1$-$C_{20}$) polyamino alkyl. In another embodiment, R is ($C_1$-$C_6$) polyhydroxy alkyl or ($C_1$-$C_6$) polyamino alkyl. In one embodiment, R is ($C_1$-$C_6$) polyhydroxy alkyl. In another embodiment, R is ($C_1$-$C_6$) polyamino alkyl. In one embodiment, R is —$CH_2CH_2OH$ or —$CH_2(CHOH)CH_2OH$. In another embodiment, R is —$CH_2CH_2NH_2$ or —$CH_2(CHNH_2)CH_2NH_2$.

In one embodiment, Y—R is —OH or —O—$R_2SO_3$. In one aspect, Y—R is OH. In another, Y—R is —O—$R_2SO_3^-$.

In one embodiment, the compound of formula 9 is a compound of formula 9a or a compound of formula 9b.

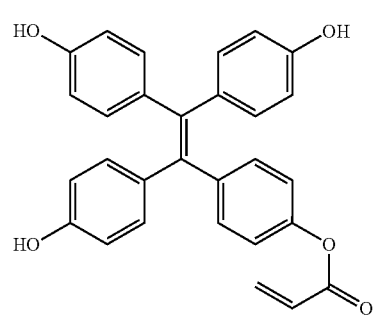

9a

-continued

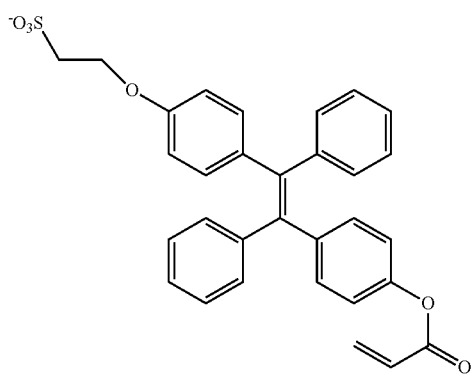
9b

In one embodiment, the compound of formula 10 is a compound of formula 10a

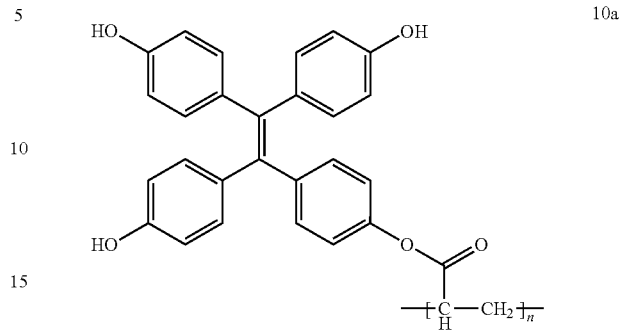
10a

In some embodiments, the apparatus further comprises a polymer. A suitable polymer is (ethane-1, 2-diylbis(oxy))bis(ethane-2,1-diyl) bis(2-methylacrylate).

Another suitable polymer is a compound of formula 10:

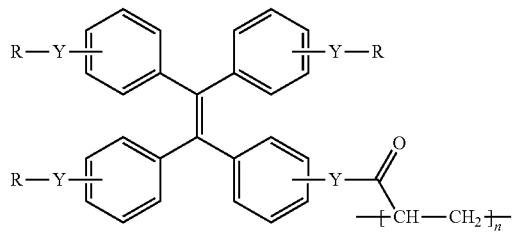
10 wherein,

Y, R, $R_1$, and $R_2$ are as defined above for compound of formula 9; and n is an integer selected from 2 to 2,000.

In one embodiment, Y is O, S or NH. In another embodiment, Y is O. In another embodiment, Y is S. In another embodiment, Y is NH. In another embodiment, Y is $NR_1$.

In one embodiment, R is H, $R_2SO_3$ or a carbohydrate. In another embodiment, R is H. In another embodiment, R is $R_2SO_3$. In another embodiment, R is a carbohydrate. In embodiments in which R is a carbohydrate, the carbohydrate is glucose, fructose, galactose, sucrose and lactose and their derivatives.

In one embodiment, R is $(C_1-C_{20})$ polyhydroxy alkyl or $(C_1-C_{20})$ polyamino alkyl. In another embodiment, R is $(C_1-C_6)$ polyhydroxy alkyl or $(C_1-C_6)$ polyamino alkyl. In one embodiment, R is $(C_1-C_6)$ polyhydroxy alkyl. In another embodiment, R is $(C_1-C_6)$ polyamino alkyl. In one embodiment, R is —$CH_2CH_2OH$ or —$CH_2(CHOH)CH_2OH$. In another embodiment, R is —$CH_2CH_2NH_2$ or —$CH_2(CHNH_2)CH_2NH_2$.

In one embodiment, Y—R is —OH or —O—$R_2SO_3$. In one aspect, Y—R is OH. In another, Y—R is —O—$R_2SO_3$.

In one embodiment, n is an integer selected from 2-20. In another embodiment, n is an integer selected from 20-200. In another embodiment, n is an integer selected from 200-2000.

The present disclosure also provides a method for preparing an apparatus for detecting nucleic acids. The method comprises (a) attaching a capture DNA probe to a surface, wherein the capture DNA probe comprises a functional group capable of attaching to the surface and comprises a sequence that is partially complementary to a first portion of a sequence of target nucleic acid; (b) contacting the target RNA with the capture DNA probe attached to the surface from step (a), wherein the first portion of the target nucleic acid partially hybridizes to the capture DNA probe; and (c) contacting a nanoparticle with the product of step (b), wherein the nanoparticle comprises a radical initiator and a detector DNA probe, the detector DNA probe comprising a sequence that is partially complementary to a second portion of the sequence of target nucleic acid, and wherein the detector DNA probe of the nanoparticle partially hybridizes to the second portion of the target nucleic acid.

The present disclosure also provides a method for detecting nucleic acid in a sample. The method comprises (a) contacting a monomer with an apparatus as herein described; (b) exposing the product of step (a) to light; and (c) detecting the presence of a polymer, wherein the presence of polymer indicates nucleic acid in the sample.

The polymer in step (c) can be detected by methods known in the art. Suitable methods include determining the density of the polymer, measuring light absorption or measuring fluorescent intensity.

In the embodiments described herein, the target nucleic acid is RNA in one aspect and DNA in another aspect.

Figure 5:
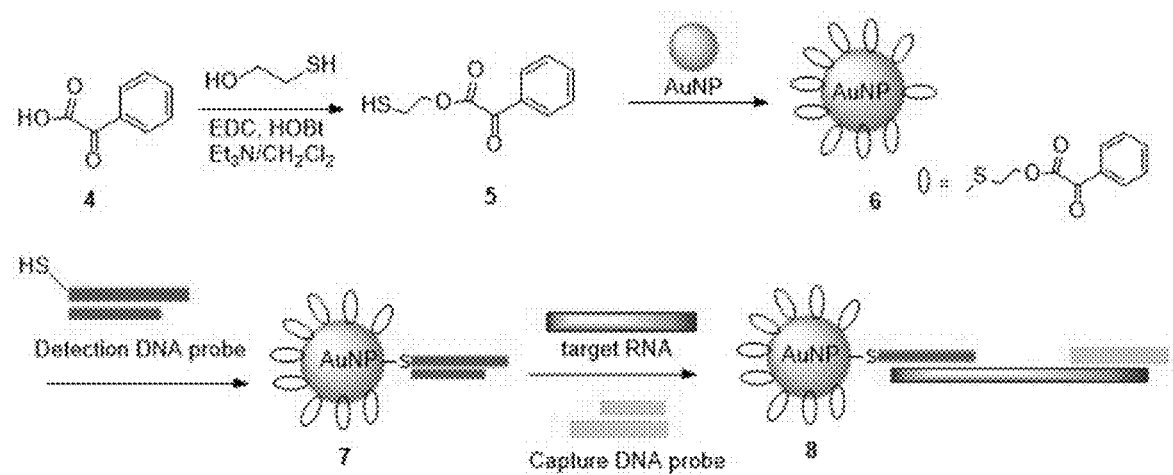
FIG. 5 shows a schematic diagram of a method to prepare gold nanoparticle complex according to one embodiment of the present disclosure.
Figure 6:
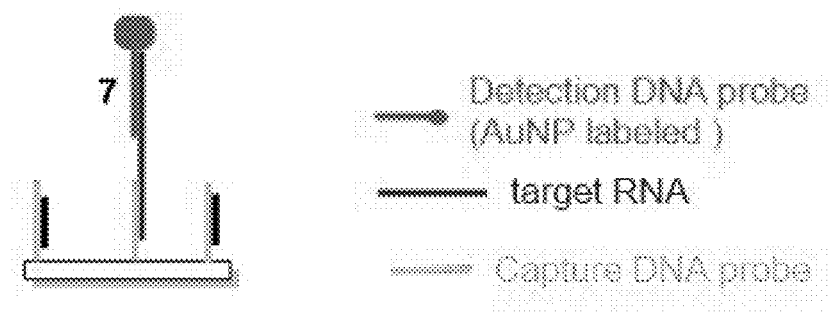
FIG. 6 shows a schematic diagram of a method to detect RNA according to one embodiment of the present disclosure.
Figure 6:
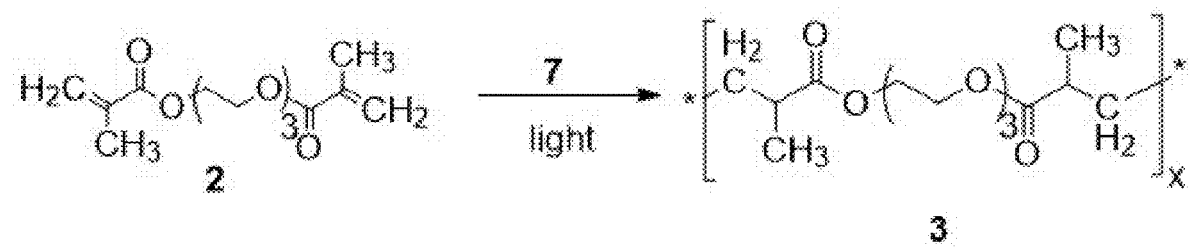

In the methods for detecting nucleic acid, and as shown in FIG. 5, a gold nanoparticle (AuNP, 7) containing a DNA and multiple copies of a-oxo-phenylacetate side chain, is prepared; the latter is an effective radical generator by UV irradiation. The detection DNA probe in the AuNP 7 specifically targeted a viral RNA and annealed to the RNA at room temperature via a toehold mediated replacement reaction. Using the same strategy, a capture DNA also anneals with the viral RNA to form the complex 8. The viral RNA detection is shown in FIG. 6, a single-stranded viral RNA was captured by its respective DNA capture probe at room temperature for 10 min via a toehold replacement reaction. After rinsing with water, the viral RNAs are retained on the glass plate. Then a solution containing AuNP 7 is added to the glass plate and incubated at room temperature for 10 min. The DNA sequence in AuNP 7 is complementary to a viral RNA region. After removing the reaction mixture containing the unbound complex and rinsing once, the spot(s) without viral RNA do not contain any initiator. Then the glass plate is dipped into a solution comprising monomer 2 and irradiated by sunlight to initiate the radical chain reactions. After irradiation for 15 min, the resulting polymer 3 is visually monitored as the detection results.

Figure 10:
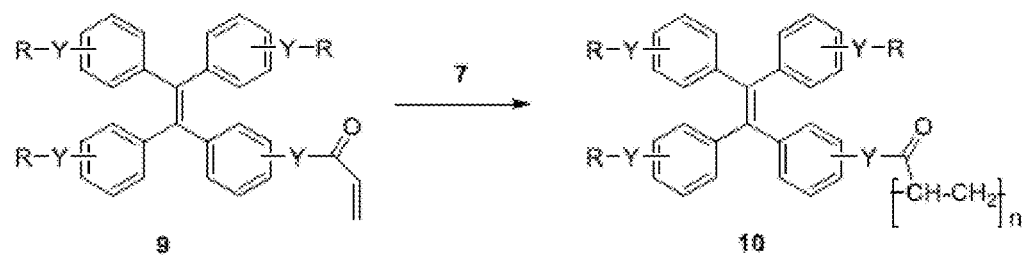
FIG. 10 shows a synthetic scheme for generating a fluorescent signal using a nanoparticle according to one embodiment of the disclosure.

Alternatively, and as shown in FIG. 10, the glass plate is dipped into a solution comprising monomer 9 and irradiated by sunlight or UV to initiate the radical chain reactions. After irradiation for about 1 to about 15 min, the resulting polymer 10 is strongly fluorescent and is visually monitored as the detection results. (J. Mei, N. L. Leung, R. T. Kwok, J. W. Lam, and B. Z. Tang. Chem Rev. 2015, 115, 11718-940.)

Compounds of Formula (I)

The present disclosure provides a compound of formula (I):

wherein:
A is an initiator;
B is a linker; and
C is a detector DNA probe, the DNA detector probe comprising a sequence that is capable of partially hybridizing to a target nucleic acid.

A is an initiator. An initiator is any moiety that can generate a radicals, such as halogens, azo compounds (R—N═N—R'), di-tert-butyl peroxide, and Benzoyl peroxide ($(PhCOO)_2$).

B is a linker. A linker is any moiety that can attach the initiator to DNA, such as small molecule compounds containing amine, hydroxy, carboxyl groups, polymers or nanoparticles.

C is a detector DNA probe and the DNA detector probe comprises a sequence that is capable of partially hybridizing to a target nucleic acid.

In one embodiment, the compound of formula (I) is:

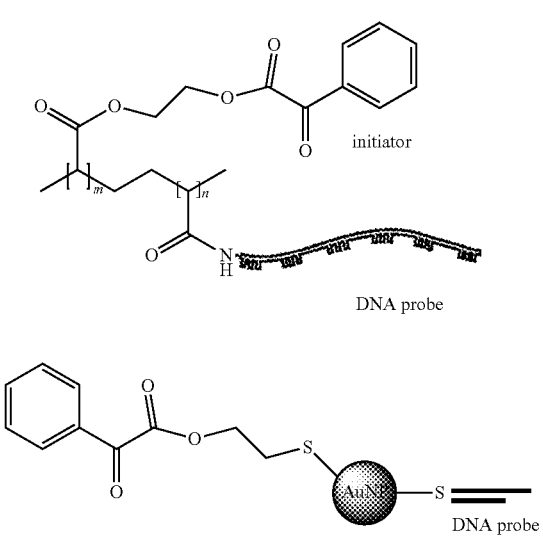

Apparatuses Comprising Compounds of Formula (I) and Methods of Preparing and Using Them The present disclosure also provides an apparatus comprising: (a) a surface for attaching a DNA capture probe; (b) the capture DNA probe; (c) a target nucleic acid, wherein a portion of the target nucleic acid sequence is partially complementary to the sequence of the capture DNA probe; and (d) the compound of formula (I) as described herein.

The surface for attaching the DNA capture probe is any surface capable of attaching DNA. Suitable surfaces that may be used include, but are not limited to, glass, nitrocellulose membrane, polyvinylidene fluoride membrane, and cellulose paper. In one embodiment, the surface for attaching the DNA capture probe is glass.

In some embodiments, the apparatus further comprises a monomer comprising a moiety selected from the group consisting of an ethylene group, fluoroethylene group, vinyl chloride group, styrene group, and epoxide group. The monomer is any compound that can form a polymer. A suitable monomer is (ethane-1, 2-diylbis(oxy))bis(ethane-2, 1-diyl) bis(2-methylacrylate). Another suitable monomer is a compound of formula 9, as described above.

In some embodiments, the apparatus further comprises a polymer. A suitable polymer is (ethane-1, 2-diylbis(oxy))bis (ethane-2,1-diyl) bis(2-methylacrylate). Another suitable polymer is a compound of formula 10, as described above.

The present disclosure also provides a method for preparing an apparatus for detecting nucleic acids. The method comprises (a) attaching a capture DNA probe to a surface, wherein the capture DNA probe comprises a functional group capable of attaching to the surface and comprises a sequence that is partially complementary to a first portion of a sequence of target nucleic acid; (b) contacting the target nucleic acid with the capture DNA probe attached to the surface from step (a), wherein the first portion of the target nucleic acid partially hybridizes to the capture DNA probe; and (c) contacting the compound of formula (I) with the product of step (b), wherein the detector DNA probe partially hybridizes to the second portion of the target nucleic acid.

The present disclosure also provides a method for detecting nucleic acid in a sample. The method comprises (a) contacting a monomer with the apparatus of as described in this section; (b) exposing the product of step (a) to light; and (c) detecting the presence of a polymer, wherein the presence of polymer indicates nucleic acid in the sample.

In the embodiments described herein, the target nucleic acid is RNA in one aspect and DNA in another aspect.

In the method for detecting nucleic acid in a sample, a chemical radical chain reaction is performed to amplify a visual signal instead of PCR reactions. In one embodiment, and as shown in FIG. 1, polymer (1), containing a DNA and multiple copies of a-oxo-phenylacetate side chain, is prepared; the latter is an effective radical generator by UV irradiation. For the detection, a single-stranded RNA is captured by its respective DNA capture probe. After rinsing with water, the viral RNAs is retained on the glass plate. Then a solution containing polymer 1 is added to the glass plate and incubated. The DNA sequence in polymer 1 is complementary to a different RNA region. After removing the reaction mixture containing unbound complex and rinsing once, the spot(s) without viral RNA does not contain any initiator. Then the plate is treated with a solution containing monomer 2 and irradiated by visible light to initiate the radical chain reactions. After irradiation, the plate is rinsed with water to remove the unreacted monomer. The resulting polymer 3 attaches itself to the surface of the plate. A few to thousands of RNA molecules of each sample are expected to be detected by this method. In one embodiment, the method can detect from about 10 to about 1,000 copies of RNA molecules. In another embodiment, the method can detect about 10, about 20, about 30, about 40, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, about 1,000, about 1,500, about 2,000, about 2,500, about 3,000, about 3,500, about 4,000, about 4,500, about 5,000, about 5,550, about 6,000, about 6,500, about 7,000, about 7,500, about 8,000, about 8,500, about 9,000, about 9,500 and about 10,000 copies of RNA molecules.

In order that this invention be more fully understood, the following examples are set forth. These examples are for the purpose of illustration only and are not to be construed as limiting the scope of the invention in any way.

EXAMPLES

Example 1

Synthesis of macromolecule 1

One mg/mL solution of N-hydroxysuccinimide (NHS) (Aldrich) in 0.1 M 2-morpholinoethanesulfonic acid (MES) 0.5 M NaCl buffer, pH 6, and a 1 mg/mL solution of the initiator 2-hydroxyethyl 2-oxo-2-phenylacetate in DMSO, were prepared and placed on a vortexer for 10 min until fully dissolved. 0.8 mg of poly(acrylic acid co-acrylamide) (200,000 MW, Aldrich) and 1 mg of the coupling agent 1-ethyl-3-(3-dimethylaminopropyl)-carbodiimide (EDC) (Aldrich) were weighed out during this time. 260 μL of the NHS solution was pipetted into the tube containing 0.8 mg of poly(acrylic acid co-acrylamide). 1 mL of MES buffer was quickly added to the tube containing 1 mg EDC, and 440 μL of this solution was quickly added to the tube containing NHS and poly(acrylic acid co-acrylamide). This solution was placed on a shaker on a low setting for 15 min to allow time for activation of the carboxylic acids of poly(acrylic acid co-acrylamide) by EDC and NHS. 685 μL of the initiator solution was added to the activated poly(acrylic acid co-acrylamide) solution, and the reaction was allowed to proceed on a shaker on a low setting for one hour and 45 min. At this time, the high-molecular-weight product was separated from unreacted smaller molecules using a 100,000-molecular-weight cut-off filter (Millipore) and a centrifuge. The spin rates and times recommended by Millipore were used. Purified products were brought up to 500 μL total volume with MES buffer, and ultraviolet spectra were collected.

Example 2

Confirmation of Polymerization

To a solution of 5% monomers in $H_2O$/dioxane (1:1), was added a different amount of initiators. The mixture was treated with UV at rt for 1 min. The results were imaged.

Results

Current RT-PCR methods for virus detection are costly and time consuming, since these methods require amplification of the viral RNA/DNA using enzyme catalyzed chain reactions.[8-13]

Figure 2:
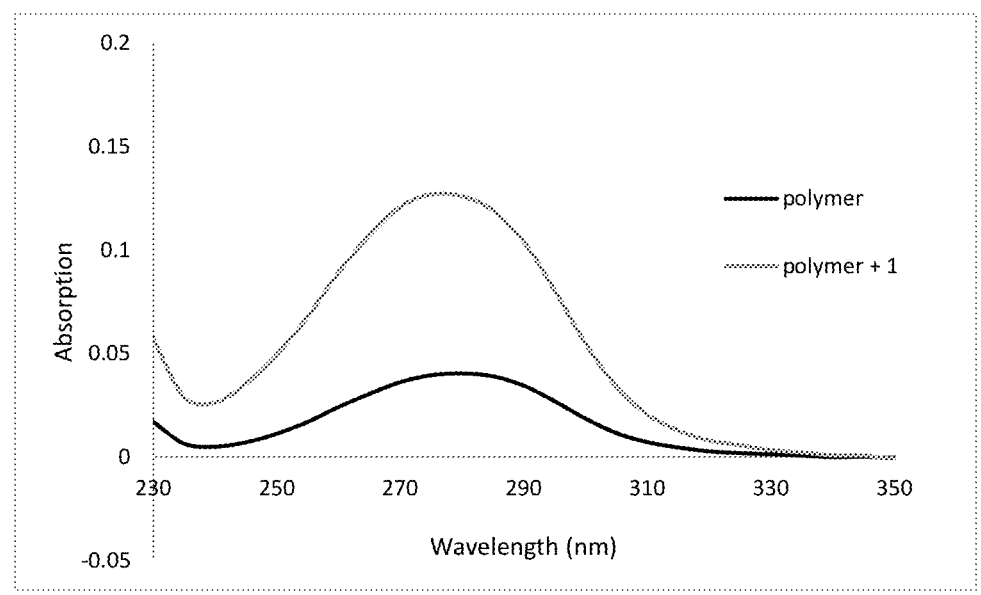
FIG. 2 shows the coupling result for the reaction depicted in FIG. 1. Activated acid with NHS and EDC in DMF. Then coupled with initiator 2-hydroxyethyl 2-oxo-2-phenylacetate in MES buffer. The excess of 2-hydroxyethyl 2-oxo-2-phenylacetate was removed using a G-25 column.
Figure 3:
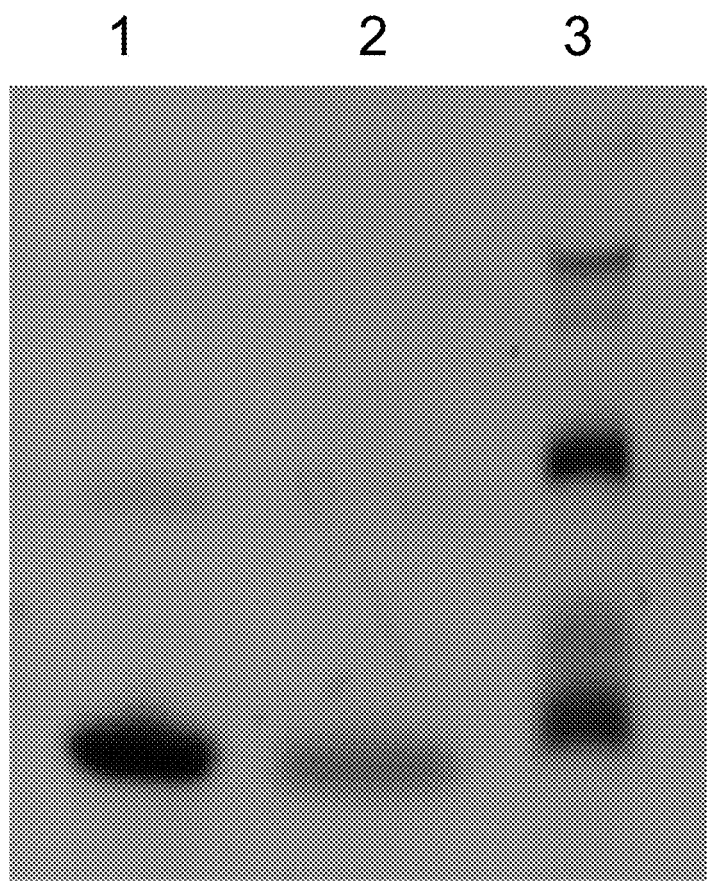
FIG. 3 shows a PAGE gel to check the coupling reaction of poly(acrylic acid) with 5'-$NH_2$-DNA. Lane 1. DNA; lane 2, DNA+2-hydroxyethyl 2-oxo-2-phenylacetate; lane 3, DNA+polymer+2-hydroxyethyl 2-oxo-2-phenylacetate.

In this study, a radical chain reaction was used to amplify a visual signal instead of PCR reactions. Firstly, we tried to couple an initiator, 2-hydroxyethyl 2-oxo-2-phenylacetate to a poly(acrylic acid) to form a multi-copies initiators in one molecule (FIG. 1). During the coupling reaction, we added 1:100 molecules of DNA compared to the ratio of initiators. As shown in FIG. 1 and FIG. 2, both the initiator and DNA were coupled to the polymer.

Figure 4:
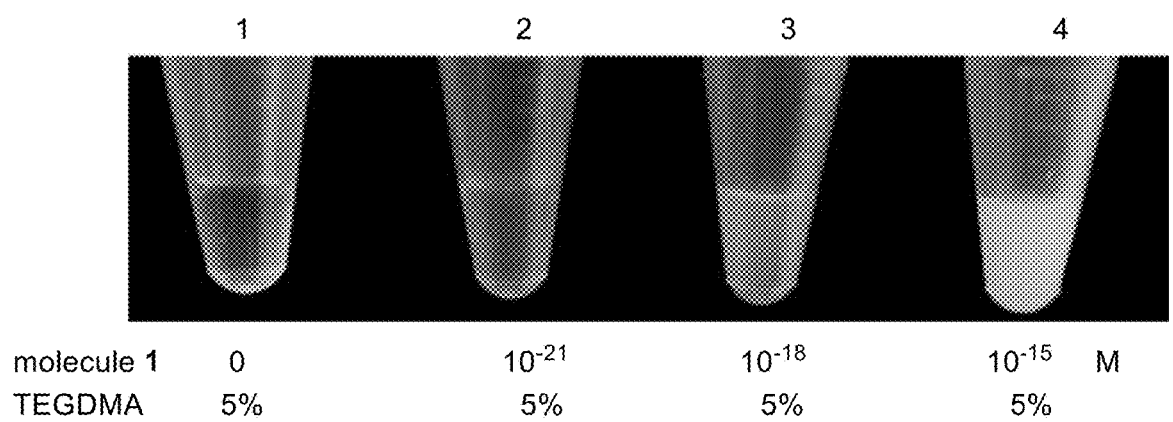
FIG. 4 shows a polymerization result for the reaction depicted in FIG. 1.

To check the chemical chain reaction, the triethylene glycol dimethacrylate (TEGDMA, 5% in $H_2O$/dioxane (1/2)) was treated with UV for 1 min in the presence of macromolecule 1 to form the polymer 3 (FIG. 1). Macromolecule 1 was very sensitive for this reaction. The lowest concentration to initiate the chain reaction was as low as $1.8 \times 10^{-21}$ M (FIG. 4), which means that about one thousand copies of RNA can be detected using this method. This will be developed into a low cost, rapid diagnostic, high specificity and high sensitivity tool for the diagnosis of RNAs.

Example 3

Synthesis of Compound 5

To a solution of benzoylformic acid (4, 150 mg, 1 mmol) in 20 mL $CH_2Cl_2$ was added 1-ethyl-3-(3-dimethylaminopropyl)-carbodiimide (EDC, 250 mg, 1.6 mmol), hydroxybenzotriazole (HOBt, 220 mg, 1.6 mmol) triethylamine (Et3N, 160 mg, 1.6 mmol) and 2-mercaptoethanol (100 mg, 1.3 mmol). The reaction mixture was stirred at room temperature for overnight in dark, then was extracted with 20 mL of 1 M HCl. The organic layer was dried with $MgSO_4$ and concentrated to dryness under diminished pressure, affording a crude residue. The crude product was purified on a flash silica gel column (20×2 cm) using 1:5 ethyl acetate/hexane for elution to obtain 5 as a colorless oil: yield 75 mg (36%).

Example 4

Preparation of gold nanoparticle 6 coupling with compound 5.

To a solution of 100 μL 13 nm gold nanoparticle (10 nM) was added 2-6 μL compound 5 (1 μM in DMSO). The reaction mixtures were shaken at room temperature for overnight in dark, then were centrifuged at 12,000 g for 20 min. The pellets were washed with 100 μL water and centrifuged again. After removing the supernatant, the pellets were resuspended in 100 μL water and stored at 4° C.

Example 5

Preparation of gold nanoparticle 7 coupling with compound 5 and detection DNA.

A solution of 10 μL DNA1 (1 μM) and DNA2 (1 μM) in 1×PBS buffer was heated at 90° C. for 5 min. After cooling at room temperature for 30 min, the mixture was added into 100 μL gold nanoparticle 6 and incubated at room temperature for 1 h. Then 100 μL 40 mM citrate-HCl, pH 3.0 was added to this reaction mixture and continue to incubate at room temperature for overnight in dark. The mixture was centrifuged at 12,000 g for 20 min. The pellets were washed with 100 μL water and centrifuged again. After removing the supernatant, the pellets were resuspended in 50 μL 1×PBS buffer and stored at 4° C. The sequences of DNAs are listed in Table 1.

TABLE 1

DNA and RNA sequences used in this example.

| Name | Sequence |
|---|---|
| Detection DNA (DNA1) | 5'-TTG CAC CAA CAG TCA ATG TCT TCA GGT TC-SH-3'<br>SEQ ID NO: 1 |
| D-Protector DNA (DNA2) | 5'-CCT GAA GAC ATT GAC TGT TGG-3'<br>SEQ ID NO: 2 |
| Capture DNA (DNA3) | 5'-$NH_2$-TT CGC CAC AAG GGC CAT GAA CAG-3'<br>SEQ ID NO: 3 |

TABLE 1-continued

DNA and RNA sequences used in this example.

| Name | Sequence |
|---|---|
| C-Protector DNA (DNA4) | 5'-TTC ATG GCC CTT GTG GCG-3' SEQ ID NO: 4 |
| Target RNA | 5'-CCU GAA GAC AUU GAC UGU UGG UGC AAU UCU GUU CAU GGC CCU UGU GGC G-3' SEQ ID NO: 5 |

Example 6

Preparation of gold nanoparticle 8.

To a solution of gold nanoparticle 7 in 10 μL 1×PBS buffer was added 2 μL of 200 nM target RNA and 2 μL of 200 nM annealed DNA3/DNA4. This reaction mixture was incubated at room temperature for 10 min and loaded on 1% agarose gel. The gel was run in 1×TAE at 100 V for 1 h.

Example 7

Preparation of glass plate containing capture DNA probe.

On the surface of an amino (—NH$_2$) modified glass plate was loaded 100 μL of 10 mM BS3 crosslinker in water and incubated at room temperature for 30 min. After removing solution and rinsing the plate, 100 μL of 10 μM annealed DNA1/DNA2 in 1×PBS buffer was added and incubated at room temperature for 2 h. The plate was removed from the solution, rinsed and ready for use.

Example 8

Detection of viral RNA.

For the detection, 100 μL single-stranded viral RNA (60, 600 or 6000 copies in each sample) samples were loaded on the detection glass plates and cultured at room temperature for 10 min. After removing solution and rinsing the plate with 1×PBS buffer, 100 μL of 1 μM annealed DNA3/DNA4 in 1×PBS buffer was added and incubated at room temperature for 10 min. After rinsing with water, the glass plates were dipped into 100 μL of 10% monomer 2 in dioxane/H2O (2:1) and irradiated by sunlight to initiate the radical chain reactions. After irradiation for 15 min, the resulting polymer 3 was visually monitored as the detection results.

Results

Current RT-PCR methods for virus detection are costly and time consuming, since these methods require amplification of the viral RNA/DNA using enzyme catalyzed chain reactions.[8-13]

Figure 7:
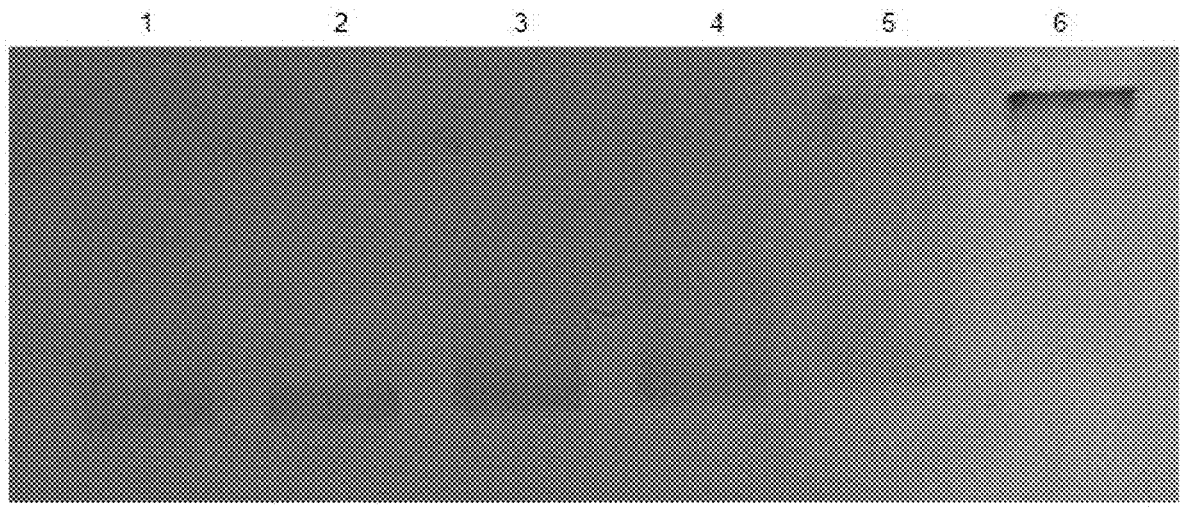
FIG. 7 shows the coupling of gold nanoparticle with different amount of compound 2 at room temperature overnight. The samples were analyzed on 1% agarose gel. The gel was run in 1×TAE at 100 V for 1 h. The nanoparticles were stabled with 10-fold unspecific DNA before loading on the gel. Lane 1, 10 nM gold nanoparticle without treatment of 2; lane 2, 10 nM gold nanoparticle with 2 µM of 2; lane 3, 10 nM gold nanoparticle with 3 µM of 2; lane 4, 10 nM gold nanoparticle with 4 µM of 2; lane 5, 10 nM gold nanoparticle with 5 µM of 2; lane 6, 10 nM gold nanoparticle with 6 µM of 2.
Figure 8:
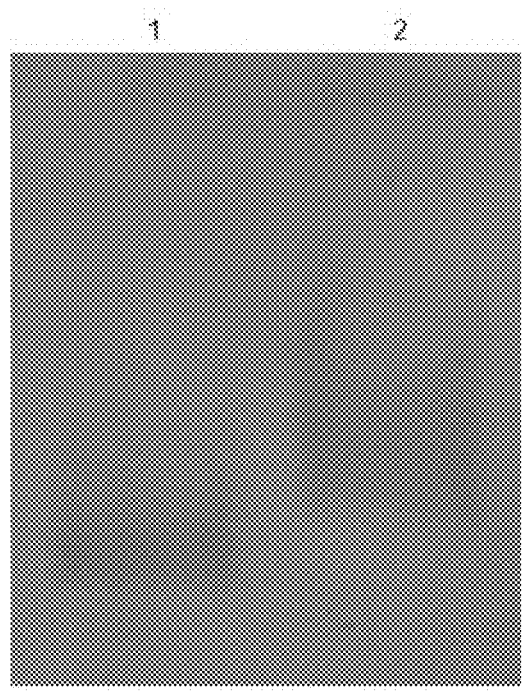
FIG. 8 shows a toehold mediated replacement reaction of DNA in gold nanoparticle 4. The reaction was carried out at room temperature for 10 min. The samples were analyzed on 1% agarose gel. The gel was run in 1×TAE at 100 V for 1 h. Lane 1, gold nanoparticle 4; lane 2, gold nanoparticle 5.
Figure 9:
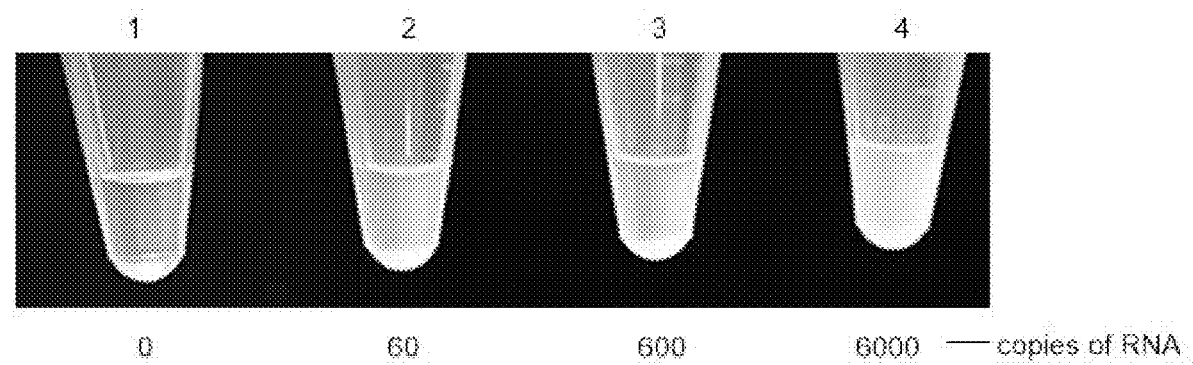
FIG. 9 shows the detection of viral RNA. Each reaction contained 100 µL solution. Different copies (0-6000) of synthesized dengue viral RNA were used to evaluate the sensitivity. After irradiation by sunlight for 15 min, the results were imaged by a cellphone camera.

As herein described, a radical chain reaction was used to amplify a visual signal instead of PCR reactions. First, 2-mercaptoethyl 2-oxo-2-phenylacetate (5), an initiator for a radical chain reaction, was synthesized. Then compound 5 was coupled with a gold nanoparticle via Au—S bond to display multi-copies of initiator on one macromolecule (6) (FIG. 5). During this coupling reaction, initiator molecules were added in excess of gold particle (200-600-fold molecules of initiator compared to gold nanoparticle). As shown in FIG. 7, when the amount of initiator is greater than 600-fold of gold-nanoparticle, it aggregated and precipitated. To obtain a stable nanoparticle, 200-fold molecules of initiators were used to prepare the gold nanoparticle 6, which was then coupled with the detection DNA to obtain the gold nanoparticle 7 (FIG. 5).

For detection, a single-stranded viral RNA was captured by its respective DNA capture probe at room temperature for 10 min via a toehold replacement reaction. After rinsing with water, the viral RNAs were retained on the glass plate. Then a solution containing AuNP 7 was added to the glass plate and incubated at room temperature for 10 min. The DNA sequence in AuNP 7 is complementary to a viral RNA region. After removing the reaction mixture containing the unbound complex and rinsing once, the spot(s) without viral RNA did not contain any initiator. Then the glass plate was dipped into a solution containing monomer 2 and irradiated by sunlight to initiate the radical chain reactions. After irradiation for 15 min, the resulting polymer 3 was visually monitored as the detection results. Using this method, tens of copies of RNA can be detected at room temperature without any additional equipment.

In summary, this study developed an equipment-free, rapid-diagnostic, low-cost, high-sensitivity and high-specificity tool for detection of RNAs. As low as tens of copies of RNAs can be detected without any additional equipment. This method also can be used to detect DNAs.

REFERENCES

The following references are hereby incorporated by reference in their entireties:

1. Erdmann, V. A., Jurga, S. and Barciszewski, J. (2015). RNA and DNA diagnostics, RNA technologies. Switzerland, Springer International Publishing.

2. Watts, J. M., Dang, K. K., Gorelick, R. J., Leonard, C. W., Bess, J. W., Jr., Swanstrom, R., Burch, C. L. and Weeks, K. M. (2009). Architecture and secondary structure of an entire HIV-1 RNA genome. *Nature* 460, 711-716, PMCID: 2724670.

3. Guzman, M. G., Halstead, S. B., Artsob, H., Buchy, P., Farrar, J., Gubler, D. J., Hunsperger, E., Kroeger, A., Margolis, H. S., Martinez, E., Nathan, M. B., Pelegrino, J. L., Simmons, C., Yoksan, S. and Peeling, R. W. (2010). Dengue: a continuing global threat. *Nat. Rev. Microbiol.* 8, S7-16, PMCID: 4333201.

4. Sharma, A. and Lal, S. K. (2017). Zika Virus: Transmission, Detection, Control, and Prevention. *Front. Microbiol.* 8, 110, PMCID: 5290000.

5. Cristina, J. and Costa-Mattioli, M. (2007). Genetic variability and molecular evolution of hepatitis A virus. *Virus. Res.* 127, 151-157.

6. Martell, M., Briones, C., de Vicente, A., Piron, M., Esteban, J. I., Esteban, R., Guardia, J. and Gomez, J. (2004). Structural analysis of hepatitis C RNA genome using DNA microarrays. *Nucleic. Acids. Res.* 32, e90, PMCID: 443556.

7. McCauley, J. W. and Mahy, B. W. (1983). Structure and function of the influenza virus genome. *Biochem J.* 211, 281-194, PMCID: 1154358.

8. Shu, P. Y. and Huang, J. H. (2004). Current advances in dengue diagnosis. *Clin. Diagn. Lab Immunol.* 11, 642-650, PMCID: 440621.

9. Lanciotti, R. S., Calisher, C. H., Gubler, D. J., Chang, G. J. and Vorndam, A. V. (1992). Rapid Detection and Typing of Dengue Viruses from Clinical-Samples by Using Reverse Transcriptase-Polymerase Chain-Reaction. *J. Clin. Microbiol.* 30, 545-551.

10. Callahan, J. D., Wu, S. J., Dion-Schultz, A., Mangold, B. E., Peruski, L. F., Watts, D. M., Porter, K. R., Murphy, G. R., Suharyono, W., King, C. C., Hayes, C. G. and Temenak, J. J. (2001). Development and evaluation of serotype- and group-specific fluorogenic reverse transcriptase PCR (TaqMan) assays for dengue virus. *J. Clin. Microbiol.* 39, 4119-4124, PMCID: PMC88496.

11. Wu, S. J. L., Lee, E. M., Putvatana, R., Shurtliff, R. N., Porter, K. R., Suharyono, W., Watts, D. M., King, C. C., Murphy, G. S., Hayes, C. G. and Romano, J. W. (2001). Detection of dengue viral RNA using a nucleic acid sequence-based amplification assay. *J. Clin. Microbiol.* 39, 2794-2798.

12. Lee, J., Hong, M. H., Han, S., Na, J., Kim, I., Kwon, Y. J., Lim, Y. B. and Choi, H. J. (2016). Sensitive and Selective Detection of HIV-1 RRE RNA Using Vertical Silicon Nanowire Electrode Array. *Nanoscale Res. Lett.* 11, 341, PMCID: 4958096.

13. LaGier, M. J., Scholin, C. A., Fell, J. W., Wang, J. and Goodwin, K. D. (2005). An electrochemical RNA hybridization assay for detection of the fecal indicator bacterium *Escherichia coli*. *Mar. Pollut. Bull.* 50, 1251-1261, PMCID: 2748388.

14. Fu, C. L., Liu, C., Wang, S., Luo, F., Lin, Z. Y. and Chen, G. N. (2016). A signal-on homogeneous electrochemical biosensor for sequence-specific microRNA based on duplex-specific nuclease-assisted target recycling amplification. *Anal. Methods* 8, 7034-7039.

15. Das, J., Ivanov, I., Montermini, L., Rak, J., Sargent, E. H. and Kelley, S. O. (2015). An electrochemical clamp assay for direct, rapid analysis of circulating nucleic acids in serum. *Nat. Chem.* 7, 569-575.

16. Wu, J., Campuzano, S., Halford, C., Haake, D. A. and Wang, J. (2010). Ternary surface monolayers for ultrasensitive (zeptomole) amperometric detection of nucleic acid hybridization without signal amplification. *Anal. Chem.* 82, 8830-8837, PMCID: 3038188.

17. Kwakye, S., Goral, V. N. and Baeumner, A. J. (2006). Electrochemical microfluidic biosensor for nucleic acid detection with integrated minipotentiostat. *Biosens. Bioelectron.* 21, 2217-2223.

18. Alter, H. J., Sanchez-Pescador, R., Urdea, M. S., Wilber, J. C., Lagier, R. J., Di Bisceglie, A. M., Shih, J. W. and Neuwald, P. D. (1995). Evaluation of branched DNA signal amplification for the detection of hepatitis C virus RNA. *J. Viral. Hepat.* 2, 121-132.

19. Collins, M. L., Irvine, B., Tyner, D., Fine, E., Zayati, C., Chang, C., Horn, T., Ahle, D., Detmer, J., Shen, L. P., Kolberg, J., Bushnell, S., Urdea, M. S. and Ho, D. D. (1997). A branched DNA signal amplification assay for quantification of nucleic acid targets below 100 molecules/ml. *Nucleic Acids Res.* 25, 2979-2984, PMCID: 146852.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed is:

1. An apparatus comprising:
    (a) a surface for attaching a DNA capture probe;
    (b) the capture DNA probe;
    (c) a target nucleic acid, wherein a first portion of the target nucleic acid sequence is partially complementary to the sequence of the capture DNA probe;
    (d) a nanoparticle for detecting nucleic acids comprising (i) a nanoparticle; (ii) a radical initiator attached to the nanoparticle; and (iii) a detector DNA attached to the nanoparticle, wherein the detector DNA has a sequence that is partially complementary to a second portion of sequence of a target nucleic acid; and
    (e) a monomer, wherein the monomer is (ethane-1,2-diylbis(oxy))bis(ethane-2,1-diyl) bis(2-methylacrylate).

2. A method for preparing the apparatus of claim 1, the method comprising:
    (a) attaching a capture DNA probe to a surface, wherein the capture DNA probe comprises a functional group capable of attaching to the surface and comprises a sequence that is partially complementary to a first portion of a sequence of target nucleic acid;
    (b) contacting the target nucleic acid with the capture DNA probe attached to the surface from step (a), wherein the first portion of the target nucleic acid partially hybridizes to the capture DNA probe;
    (c) contacting a nanoparticle for detecting nucleic acids with the product of step (b), wherein the nanoparticle comprises (i) a nanoparticle; (ii) a radical initiator attached to the nanoparticle; and (iii) a detector DNA probe attached to the nanoparticle, the detector DNA probe comprising a sequence that is partially complementary to a second portion of the sequence of target nucleic acid, and wherein the detector DNA probe of the nanoparticle partially hybridizes to the second portion of the target nucleic acid; and
    (d) contacting the product of step (c) with a monomer, wherein the monomer is (ethane-1,2-diylbis(oxy))bis(ethane-2,1-diyl) bis(2-methylacrylate).

3. A method for detecting nucleic acid in a sample, the method comprising:
    (a) contacting a monomer with the apparatus of the claim 1;
    (b) exposing the product of step (a) to light; and
    (c) detecting the presence of a polymer, wherein the presence of polymer indicates nucleic acid in the sample;
wherein the nucleic acid is detected by a visual signal of polymerization of the monomer.

4. An apparatus comprising:
    (a) a surface for attaching a DNA capture probe;
    (b) the capture DNA probe;
    (c) a target nucleic acid, wherein a first portion of the target nucleic acid sequence is partially complementary to the sequence of the capture DNA probe;
    (d) a nanoparticle for detecting nucleic acids comprising (i) a nanoparticle; (ii) a radical initiator attached to the nanoparticle; and (iii) a detector DNA attached to the nanoparticle, wherein the detector DNA has a sequence that is partially complementary to a second portion of sequence of a target nucleic acid; and
    (e) a polymer, wherein the polymer is a compound of formula 10:

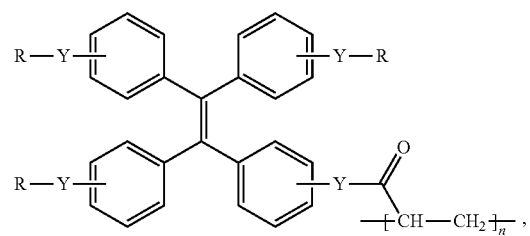

wherein
  Y is independently selected from O, S, NH or NR$_1$;
  R is independently selected from H, (C$_2$-C$_6$) alkyne, R$_2$SO$_3$, (C$_1$-C$_{20}$) polyhydroxy alkyl, (C$_{1\text{-}20}$) polyamino alkyl or carbohydrate; and
  R$_1$ and R$_2$ are independently H or (C$_1$-C$_6$) alkyl; and
  n is an integer selected from 2 to 2000.

5. An apparatus comprising:
  (a) a surface for attaching a DNA capture probe;
  (b) the capture DNA probe;
  (c) a target nucleic acid, wherein a portion of the target nucleic acid sequence is partially complementary to the sequence of the capture DNA probe;
  (d) a compound of formula (I), wherein the compound of formula (I):

A-B-C    (I), wherein:
    A is an initiator;
    B is a linker; and
    C is a detector DNA probe, the DNA detector probe comprising a sequence that is capable of partially hybridizing to a target nucleic acid; and
  (e) a monomer, wherein the monomer is (ethane-1,2-diylbis(oxy))bis(ethane-2,1-diyl) bis(2-methylacrylate).

6. A method for preparing the apparatus of claim 5, the method comprising:
  (a) attaching a capture DNA probe to a surface, wherein the capture DNA probe comprises a functional group capable of attaching to the surface and comprises a sequence that is partially complementary to a first portion of a sequence of target nucleic acid;
  (b) contacting the target nucleic acid with the capture DNA probe attached to the surface from step (a), wherein the first portion of the target nucleic acid partially hybridizes to the capture DNA probe;
  (c) contacting the compound of formula (I) with the product of step (b), wherein the detector DNA probe partially hybridizes to the second portion of the target nucleic acid and wherein the compound of formula (I) is:

A-B-C    (I), wherein:
    A is an initiator;
    B is a linker; and
    C is a detector DNA probe, the DNA detector probe comprising a sequence that is capable of partially hybridizing to a target nucleic acid; and
  (d) contacting the product of step (c) with a monomer, wherein the monomer is (ethane-1,2-diylbis(oxy))bis(ethane-2,1-diyl) bis(2-methylacrylate).

7. An apparatus comprising:
  (a) a surface for attaching a DNA capture probe;
  (b) the capture DNA probe;
  (c) a target nucleic acid, wherein a portion of the target nucleic acid sequence is partially complementary to the sequence of the capture DNA probe;
  (d) a compound of formula (I), wherein the compound of formula (I):

A-B-C    (I), wherein:
    A is an initiator;
    B is a linker; and
    C is a detector DNA probe, the DNA detector probe comprising a sequence that is capable of partially hybridizing to a target nucleic acid; and
  (e) a polymer, wherein the polymer is compound of formula 10:

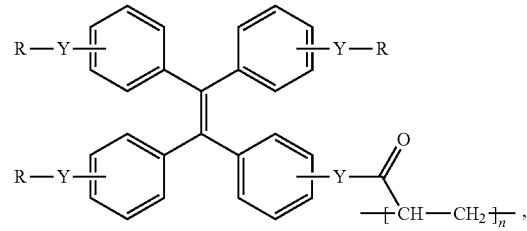

wherein
    Y is independently selected from O, S, NH or NR$_1$;
    R is independently selected from H, (C$_2$-C$_6$) alkyne, R$_2$SO$_3$, (C$_1$-C$_{20}$) polyhydroxy alkyl, (C$_1$-C$_{20}$) polyamino alkyl or carbohydrate; and
    R$_1$ and R$_2$ are independently H or (C$_1$-C$_6$) alkyl; and
    n is an integer selected from 2 to 2000.

8. An apparatus comprising:
  (a) a surface for attaching a DNA capture probe;
  (b) the capture DNA probe;
  (c) a target nucleic acid, wherein a portion of the target nucleic acid sequence is partially complementary to the sequence of the capture DNA probe;
  (d) a compound of formula (I), wherein the compound of formula (I):

A-B-C    (I), wherein:
    A is an initiator;
    B is a linker; and
    C is a detector DNA probe, the DNA detector probe comprising a sequence that is capable of partially hybridizing to a target nucleic acid; and
  (e) a polymer, wherein the polymer comprises (ethane-1,2-diylbis(oxy))bis(ethane-2,1-diyl) bis(2-methylacrylate) monomer.

9. A method for detecting nucleic acid in a sample, the method comprising:
  (a) contacting the monomer (ethane-1,2-diylbis(oxy))bis(ethane-2,1-diyl) bis(2-methylacrylate) with an apparatus, the apparatus comprising:
    (i) a surface for attaching a DNA capture probe;
    (ii) the capture DNA probe;
    (iii) a target nucleic acid, wherein a portion of the target nucleic acid sequence is partially complementary to the sequence of the capture DNA probe; and
    (iv) a compound of formula (I):

A-B-C    (I), wherein:
      A is an initiator;
      B is a linker; and
      C is a detector DNA probe, the DNA detector probe comprising a sequence that is capable of partially hybridizing to a target nucleic acid;
  (b) exposing the product of step (a) to light; and
  (c) detecting the presence of a polymer, wherein the presence of polymer indicates nucleic acid in the sample;

wherein the nucleic acid is detected by a visual signal of polymerization of the monomer.

\* \* \* \* \*

SEQUENCE LISTING

```
<160> NUMBER OF SEQ ID NOS: 5

<210> SEQ ID NO 1
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (29)..(29)
<223> OTHER INFORMATION: s2c

<400> SEQUENCE: 1
ttgcaccaac agtcaatgtc ttcaggttn                                          29

<210> SEQ ID NO 2
<211> LENGTH: 21
<212> TYPE: DNA
<213> ORGANISM: Artificial Sequence
<220> FEATURE:
<223> OTHER INFORMATION: Synthetic DNA

<400> SEQUENCE: 2
cctgaagaca ttgactgttg g                                                  21

<210> SEQ ID NO 3
<211> LENGTH: 23
<212> TYPE: DNA
<213> ORGANISM: Artificial Sequence
<220> FEATURE:
<223> OTHER INFORMATION: Sythetic DNA
<220> FEATURE:
<221> NAME/KEY: misc_feature
<222> LOCATION: (1)..(1)
<223> OTHER INFORMATION: 1-amino thymine
```

```
<400> SEQUENCE: 3
ntcgccacaa gggccatgaa cag                                    23

<210> SEQ ID NO 4
<211> LENGTH: 18
<212> TYPE: DNA
<213> ORGANISM: Artificial Sequence
<220> FEATURE:
<223> OTHER INFORMATION: Synthetic DNA

<400> SEQUENCE: 4
ttcatggccc ttgtggcg                                          18

<210> SEQ ID NO 5
<211> LENGTH: 49
<212> TYPE: RNA
<213> ORGANISM: Artificial Sequence
<220> FEATURE:
<223> OTHER INFORMATION: Synthetic DNA

<400> SEQUENCE: 5
ccugaagaca uugacuguug gugcaauucu guucauggcc cuuguggcg         49
```